United States Patent
Aoki et al.

(10) Patent No.: US 9,732,657 B2
(45) Date of Patent: Aug. 15, 2017

(54) OXYGEN SENSOR AND OXYGEN SENSOR CONTROL DEVICE

(75) Inventors: Keiichiro Aoki, Shizuoka-ken (JP); Takanori Sasaki, Toyota (JP); Go Hayashita, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 1088 days.

(21) Appl. No.: 13/993,734

(22) PCT Filed: Dec. 24, 2010

(86) PCT No.: PCT/JP2010/073427
§ 371 (c)(1),
(2), (4) Date: Jun. 13, 2013

(87) PCT Pub. No.: WO2012/086079
PCT Pub. Date: Jun. 28, 2012

(65) Prior Publication Data
US 2013/0276431 A1  Oct. 24, 2013

(51) Int. Cl.
*F01N 11/00* (2006.01)
*G01N 27/407* (2006.01)
*F02D 41/12* (2006.01)
*F02D 41/14* (2006.01)
*F02D 41/20* (2006.01)

(52) U.S. Cl.
CPC .......... *F01N 11/007* (2013.01); *F02D 41/123* (2013.01); *F02D 41/1454* (2013.01);
(Continued)

(58) Field of Classification Search
CPC ..... F01N 11/007; G01N 27/407–27/41; F02D 41/1454–41/1455; F02D 41/1476; F02D 41/123; F02D 2041/2051
(Continued)

(56) References Cited

U.S. PATENT DOCUMENTS

| 4,264,425 A | * | 4/1981 | Kimura | G01N 27/417 204/412 |
| 4,304,652 A | * | 12/1981 | Chiba | G01N 27/4071 204/425 |

(Continued)

FOREIGN PATENT DOCUMENTS

| JP | 62-231156 | 10/1987 |
| JP | 5-18938 | 1/1993 |

(Continued)

*Primary Examiner* — Mark Laurenzi
*Assistant Examiner* — Mickey France
(74) *Attorney, Agent, or Firm* — Finnegan, Henderson, Farabow, Garrett & Dunner, LLP

(57) ABSTRACT

In this invention, an EMF oxygen sensor is subjected to an activation process applying unidirectional voltage between an atmosphere electrode and an exhaust electrode thereof. A control device controlling the oxygen sensor in which a voltage was applied with the atmosphere electrode being positive, additionally applies unidirectional voltage between the electrodes to make the atmosphere electrode positive, for example, when the oxygen sensor was used under an environment in which the air-fuel ratio of the internal combustion engine was rich relative to the theoretical air-fuel ratio. Conversely, a control device controlling the oxygen sensor in which a voltage was applied to make the atmosphere electrode negative, additionally applies unidirectional voltage between the electrodes to make the atmosphere electrode negative, for example, when the oxygen sensor was used under an environment in which the air-fuel ratio was lean relative to the theoretical air-fuel ratio.

12 Claims, 2 Drawing Sheets

(52) U.S. Cl.
CPC ....... *F02D 41/1476* (2013.01); *G01N 27/407* (2013.01); *F02D 2041/2051* (2013.01)

(58) Field of Classification Search
USPC .......... 60/276, 277, 285, 286; 73/1.02, 1.06, 73/23.31, 114.69, 114.71, 114.73, 23.3; 701/29.7–31.3
See application file for complete search history.

(56) References Cited

U.S. PATENT DOCUMENTS

| | | | | |
|---|---|---|---|---|
| 4,391,691 | A * | 7/1983 | Linder | F02D 41/1476 204/408 |
| 5,433,830 | A | 7/1995 | Kawai et al. | |
| 6,286,306 | B1 * | 9/2001 | Takakura | B01D 53/9454 60/286 |
| 2005/0252788 | A1 * | 11/2005 | Farber | G01N 27/4071 205/687 |
| 2006/0065256 | A1 * | 3/2006 | Katoh | F02D 41/2454 123/674 |
| 2007/0101701 | A1 * | 5/2007 | Acke | B01D 53/9431 60/286 |

FOREIGN PATENT DOCUMENTS

| | | |
|---|---|---|
| JP | 6-265522 | 9/1994 |
| JP | 7-110315 | 4/1995 |

* cited by examiner

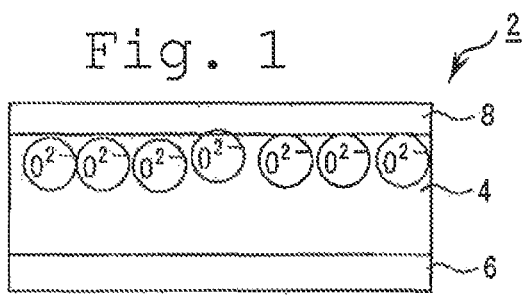
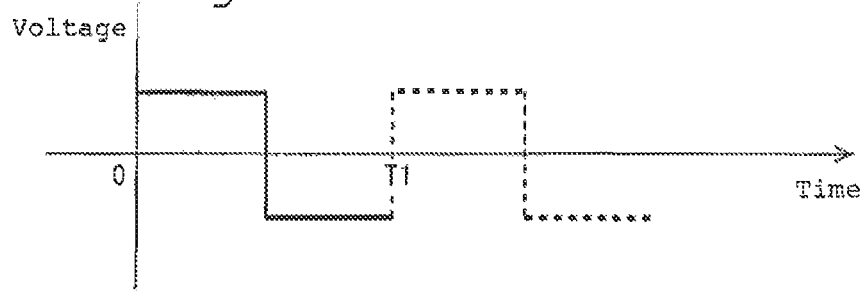
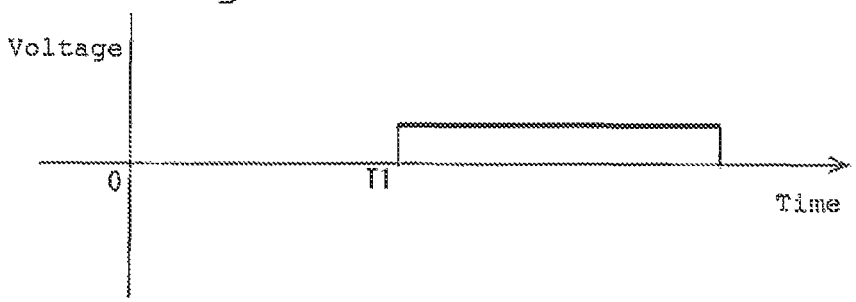
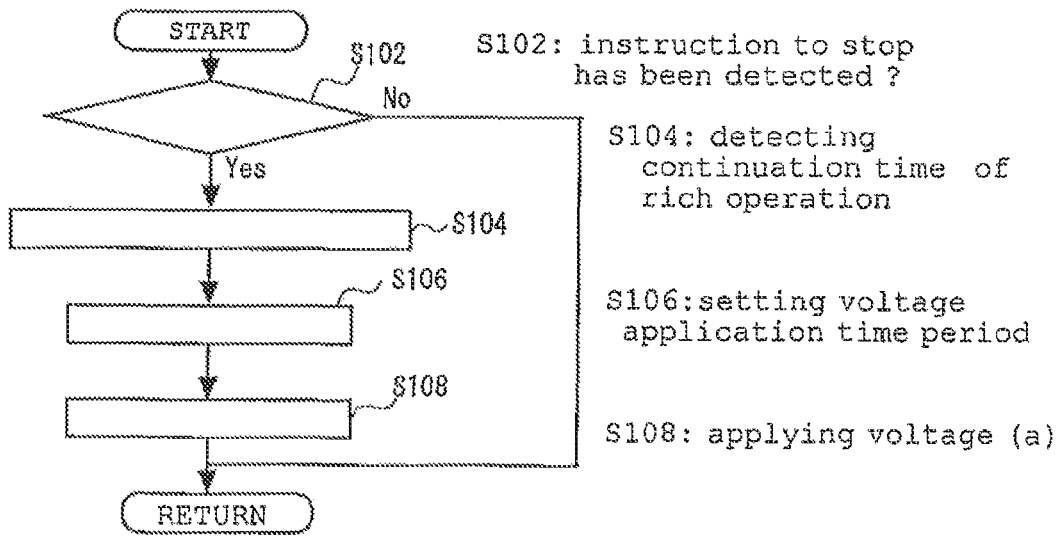

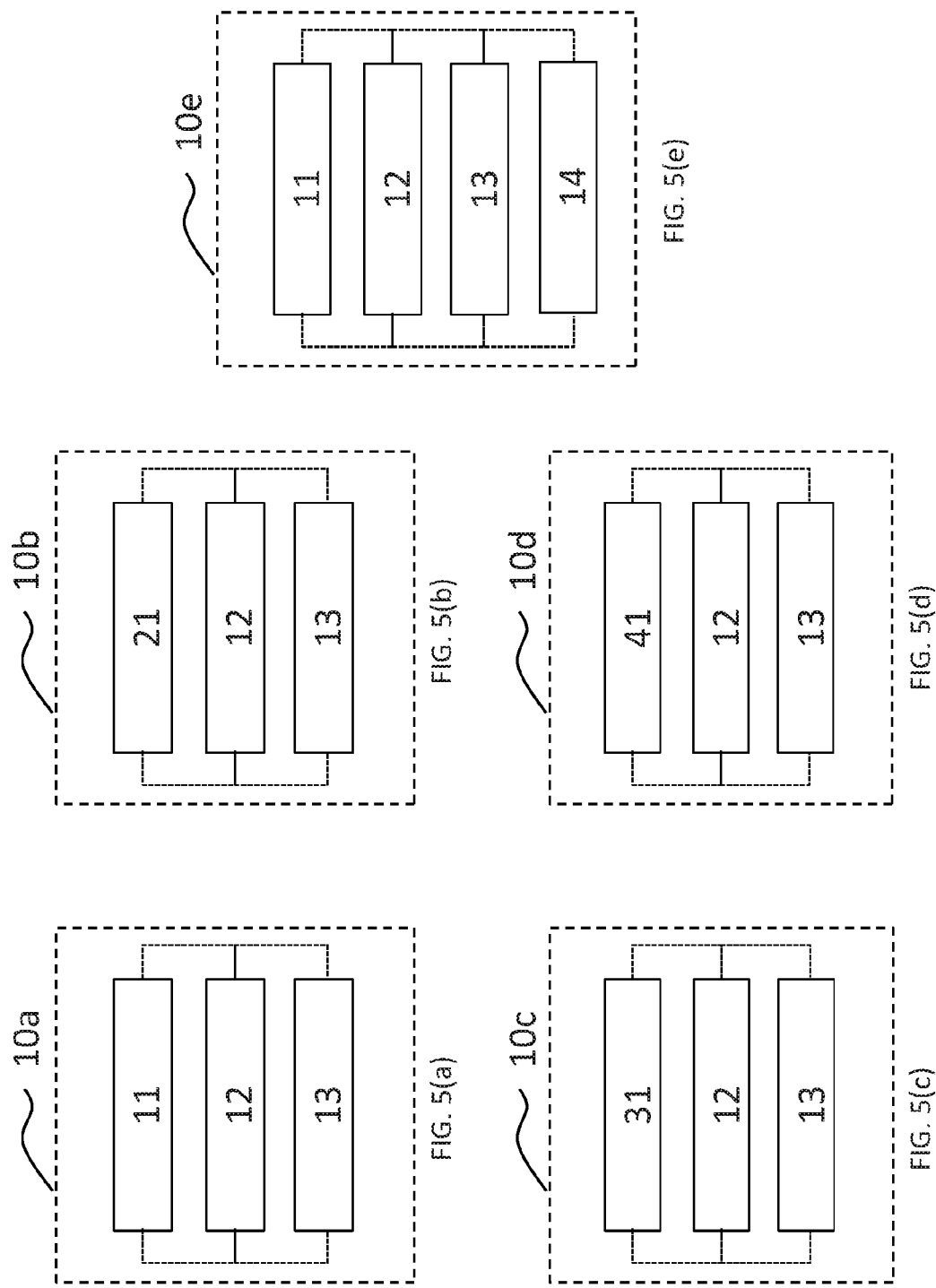

OXYGEN SENSOR AND OXYGEN SENSOR CONTROL DEVICE

CROSS-REFERENCE TO RELATED APPLICATIONS

This application is a national phase application of International Application No. PCT/JP2010/073427, filed Dec. 24, 2010, the content of which is incorporated herein by reference.

TECHNICAL FIELD

This invention relates to an oxygen sensor and an oxygen sensor control device. More specifically, this invention relates to an oxygen sensor and an oxygen sensor control device that subjects the oxygen sensor to an activation process.

BACKGROUND ART

In a known technique that is utilized for air-fuel ratio feedback control or for evaluating the oxygen storage capacity of a catalyst, an oxygen sensor is arranged downstream of a catalyst that is mounted in an exhaust passage of a vehicle to detect changes in the exhaust gas air-fuel ratio downstream of the catalyst. Thus, the oxygen sensor that is arranged downstream of the catalyst takes low-concentration exhaust gas that has been purified by the catalyst as a detection object. Accordingly, it is desirable that the oxygen sensor can detect a change in the air-fuel ratio of low-concentration gas with high sensitivity.

For example, Patent Literature 1 discloses a technique that improves the sensitivity of a limiting-current-type sensor to gas in a low-concentration range. According to the technology described in Patent Literature 1, when the detected gas is in a low-concentration range, a voltage whose polarity is opposite to the polarity of a voltage applied at a time of normal measurement is applied to electrodes of the sensor, and a current value is detected. According to the invention described in Patent Literature 1, it is thereby possible to detect the concentration of gas in a low-concentration range with high sensitivity.

PRIOR ART DOCUMENTS

Patent Document

Patent Document 1: Japanese Patent Laid-Open No. 62-231156
Patent Document 2: Japanese Patent Laid-Open No. 06-265522

SUMMARY OF INVENTION

Problem to be Solved by the Invention

A comparatively low cost electromotive force-type oxygen sensor is used as the sensor that is arranged downstream of the catalyst in a vehicle. An electromotive force-type oxygen sensor outputs an electromotive force produced by a difference between the oxygen concentrations of a pair of electrodes, and the output thereof changes significantly in a sudden manner depending on whether exhaust gas is rich or lean with respect to a theoretical air-fuel ratio.

In this respect, the sensor sensitivity improvement technique described in the aforementioned Patent Literature 1 is a technique that is applied to a limiting-current-type sensor. That is, the sensor described in Patent Literature 1 is one in which a voltage is applied in either a forward direction or a reverse direction when detecting a gas concentration, and which outputs a current value of the sensor at the time the voltage is applied. Accordingly, the technique for improving the sensitivity of a sensor described in the aforementioned Patent Literature 1 is not a technique that can be applied to an electromotive force-type oxygen sensor.

In addition, NO that is a lean component in exhaust gas has low reactivity with the electrodes of the sensor, and has low output response sensitivity. On the other hand, among rich gas components, $H_2$, $CH_4$, and CO, the rate of diffusion of $H_2$ and $CH_4$ is faster than that of the lean components ($O_2$ and $NO_x$), and the adsorption properties of CO with respect to the electrodes of the sensor are high. Consequently, there is a tendency for an oxygen sensor to be liable to output a rich output value and for the lean sensitivity thereof to easily decrease. Therefore, in some cases a bias that is caused by a sensitivity difference arises in the output of an oxygen sensor. This kind of bias in an oxygen sensor is not preferable from the viewpoint of improving air-fuel ratio control. In this respect, although the technique for improving the sensor sensitivity described in the aforementioned Patent Literature 1 is designed to improve sensitivity with respect to low-concentration gas, the technique does not improve the situation regarding a difference between the sensitivity for rich gas and the sensitivity for lean gas.

The present invention has been conceived to solve the above described problems, and an object of the present invention is to provide an control device for an oxygen sensor that has been improved so as to suppress a bias in sensitivity with respect to rich gas and lean gas of an electromotive force-type oxygen sensor and thereby improve the sensitivity of the oxygen sensor.

Means for Solving the Problem

An oxygen sensor of the present invention is an electromotive force-type oxygen sensor that is disposed in an exhaust passage of an internal combustion engine. The oxygen sensor includes a solid electrolyte, an atmosphere electrode that is disposed on one face side of the solid electrolyte, and an exhaust electrode that is disposed on a face on an opposite side to the one face. The atmosphere electrode serves as an electrode that contacts with atmosphere when the oxygen sensor is disposed in the exhaust passage, and the exhaust electrode serves as an electrode contacts with exhaust gas when the oxygen sensor is disposed in the exhaust passage. The oxygen sensor of the present invention is subjected to an activation process that applies a unidirectional voltage between the atmosphere electrode and the exhaust electrode.

The unidirectional voltage is in a direction that makes the atmosphere electrode positive and makes the exhaust electrode negative or in a direction that makes that makes the atmosphere electrode negative and makes the exhaust electrode positive. Further, the unidirectional voltage is preferably a voltage in a range which does not cause blackening with respect to the solid electrolyte.

An oxygen sensor control device according to the present invention controls the above described oxygen sensor. For example, in the control device controlling an oxygen sensor being subjected to an activation process for applying a voltage in a direction to make the atmosphere electrode positive and make the exhaust electrode negative, rich operation continuation time detection means detects a continuation time of rich operation that is a time in which an air-fuel ratio is rich relative to a theoretical air-fuel ratio during a predetermined operation period of the internal combustion engine. Voltage application time period setting means sets a voltage application time period in accordance with the detected continuation time of rich operation. Thereafter, voltage application control means applies a unidirectional voltage to make the atmosphere electrode positive and make the exhaust electrode negative between the atmosphere electrode and the exhaust electrode, in accordance with the voltage application time period.

Further, for example, in a control device controlling an oxygen sensor that has been subjected to an activation process for applying a voltage in a direction to make the atmosphere electrode negative and make the exhaust electrode positive, lean operation continuation time detection means detects a continuation time of lean operation that is a time in which an air-fuel ratio is lean relative to a theoretical air-fuel ratio during a predetermined operation period of the internal combustion engine. Voltage application time period setting means sets a voltage application time period in accordance with the detected continuation time of lean operation. Thereafter, voltage application control means applies a unidirectional voltage to make the atmosphere electrode negative and make the exhaust electrode positive between the atmosphere electrode and the exhaust electrode, in accordance with the voltage application time period.

Further, for example, in a control device controlling an oxygen sensor that has been subjected to an activation process for applying a voltage in a direction to make the atmosphere electrode positive and make the exhaust electrode negative, rich operating state detection means detects a rich operating state that is a state in which the operating state of the internal combustion engine is in a predetermined high speed and high load operating range and the air-fuel ratio is in a rich amount increasing range. Thereafter, if the rich operating state is detected, voltage application means applies a unidirectional voltage between the atmosphere electrode and the exhaust electrode to make the atmosphere electrode positive and make the exhaust electrode negative.

In addition, for example, in a control device controlling an oxygen sensor being subjected to an activation process for applying a voltage in a direction to make the atmosphere electrode negative and make the exhaust electrode positive, fuel-cut operation detection means detects when an operating state of the internal combustion engine in which the oxygen sensor is disposed is a fuel-cut operation state. Further, if the fuel-cut operation detection means detects that the operating state is a fuel-cut operation state, a unidirectional voltage to make an atmosphere electrode negative and make an exhaust electrode positive is applied between the atmosphere electrode and the exhaust electrode by voltage application means.

In the oxygen sensors that these control devices control, preferably the unidirectional voltage in the activation process is a voltage in a range which does not cause blackening with respect to the solid electrolyte.

Furthermore, the control devices for an oxygen sensor according to the present invention, for example, may further include element-resistance detection means that detects or estimates an element resistance of the oxygen sensor. In this case, the voltage application means may be configured to control a size of the unidirectional voltage or an application time period of the unidirectional voltage in accordance with the element resistance.

Effects of Invention

By adopting a configuration in which a unidirectional voltage is applied between an atmosphere electrode and an exhaust electrode of an oxygen sensor, in an initial state, a difference between a sensitivity of the oxygen sensor to lean gas and a sensitivity of the oxygen sensor to rich gas can be suppressed. It is thereby possible to suppress output variations resulting from a difference in the sensitivities of the oxygen sensor.

Further, when a voltage that is applied between the atmosphere electrode and the exhaust electrode of the oxygen sensor in an activation process is applied in a direction that makes the atmosphere electrode positive and makes the exhaust electrode negative, oxygen ions can be moved from the exhaust electrode to the atmosphere electrode side by the activation process. It is thus possible to realize a state that facilitates movement of oxygen ions from the atmosphere electrode to the exhaust electrode side of the oxygen sensor. Accordingly, the sensitivity to lean gas of the oxygen sensor can be improved.

Further, in the activation process, when a voltage applied between the atmosphere electrode and the exhaust electrode of the oxygen sensor is in a direction that makes the atmosphere electrode negative and makes the exhaust electrode positive, as a result of the activation process, oxygen ions can be moved from the atmosphere electrode side to the exhaust electrode side. Thus, the oxygen ions can be caused to be biased to the exhaust electrode side, and the sensitivity of the oxygen sensor to rich gas is suppressed.

Further, by making the unidirectional voltage a voltage in a range which does not cause blackening with respect to the solid electrolyte, the performance of the solid electrolyte is not degraded by the voltage application, and an oxygen sensor in which sensitivity variations are suppressed can be obtained.

In addition, in a control device for an electromotive force-type oxygen sensor in which a voltage in a direction that makes an atmosphere electrode positive has been applied previously, for example, control is performed that, for a voltage application time period that is in accordance with a continuation time of rich operation, applies a unidirectional voltage that makes the atmosphere electrode positive and makes the exhaust electrode negative. Therefore, even when a rich environment in which an effect of improving the lean sensitivity improvement is liable to lessen has continued, the effect of a process for improving the lean sensitivity of the oxygen sensor can be maintained at a high level. Accordingly, the effect of suppressing variations in the oxygen sensor can be maintained over a long term.

Further, in a control device for an electromotive force-type oxygen sensor in which a voltage in a direction that makes an atmosphere electrode negative has been applied previously, for example, a voltage application time period is set in accordance with a continuation time of lean operation of the internal combustion engine, and control is performed in which a unidirectional voltage is applied that makes the atmosphere electrode negative and makes the exhaust electrode positive. Therefore, even in a case where a lean environment in which an effect of suppressing the rich sensitivity is liable to lessen has continued, the effect of a process for suppressing the rich sensitivity of the oxygen sensor can be maintained at a high level. Accordingly, the effect of suppressing variations in the oxygen sensor can be maintained over a long term.

In addition, in a control device for an electromotive force-type oxygen sensor in which a voltage in a direction that makes an atmosphere electrode positive has been applied previously, for example, control for applying a unidirectional voltage that makes the atmosphere electrode positive and makes the exhaust electrode negative is performed in a case where the operating state of the internal combustion engine is a predetermined rich operating state. Therefore, the lean sensitivity can be improved even under an operating environment in which an effect of improving the lean sensitivity is liable to lessen. Accordingly, the effect of suppressing variations in the oxygen sensor can be maintained over a long term.

Furthermore, in a control device for an electromotive force-type oxygen sensor in which a voltage in a direction that makes an atmosphere electrode negative has been applied previously, for example, when the operating state of the internal combustion engine is a fuel-cut operation state, control is performed in which a unidirectional voltage is applied that makes the atmosphere electrode negative and makes the exhaust electrode positive. Therefore, even under a lean operating environment in which an effect of suppressing the rich sensitivity is liable to lessen, the rich sensitivity of the oxygen sensor can be suppressed. Accordingly, the effect of suppressing variations in the oxygen sensor can be maintained over a long term.

In this connection, when element resistance increases due to aging deterioration or the like of the oxygen sensor, the amount of current that flows between the electrodes decreases even when the same voltage is applied. Accordingly, it can be considered that when element resistance has increased, even if the same voltage is applied, the above described effect of improving the lean sensitivity or suppressing the rich sensitivity will not be adequately obtained. In this regard, if the size or application time period of the voltage when applying a unidirectional voltage is controlled in accordance with the element resistance, even in a case where element resistance due to aging deterioration or the like has increased, a definite current can be caused to flow between the electrodes. Accordingly, an effect of improving the lean sensitivity or suppressing the rich sensitivity can be adequately obtained.

BRIEF DESCRIPTION OF DRAWINGS

FIG. 1 is a schematic diagram for describing an oxygen sensor according to Embodiment 1 of the present invention.

FIG. 2 is views for describing an alternating voltage applied in the Embodiment 1 of the present invention.

FIG. 3 is views for describing an unidirectional voltage applied in the Embodiment 1 of the present invention.

FIG. 4 is a flowchart for describing a routine of control that the control device executes according to Embodiment 2 of the present invention.

FIG. 5(a) is a schematic diagram for describing a first embodiment of a control device according to the present application.

FIG. 5(b) is a schematic diagram for describing a second embodiment of a control device according to the present application.

FIG. 5(c) is a schematic diagram for describing a third embodiment of a control device according to the present application.

FIG. 5(d) is a schematic diagram for describing a fourth embodiment of a control device according to the present application.

FIG. 5(e) is a schematic diagram for describing a fifth embodiment of a control device according to the present application.

MODES FOR CARRYING OUT THE INVENTION

Embodiments of the present invention are described hereunder with reference to the drawings. For each of the drawings, the same or corresponding portions are denoted by the same reference numerals, and a description of such portions is simplified or omitted.

Embodiment 1

FIG. 1 is a schematic diagram for describing an oxygen sensor according to Embodiment 1 of the present invention. An oxygen sensor 2 shown in FIG. 1, for example, is disposed on a downstream side of a catalyst in an exhaust passage of an internal combustion engine, and is used to detect changes in the air-fuel ratio of exhaust gas.

The oxygen sensor 2 shown in FIG. 1 includes a solid electrolyte membrane made of zirconia or the like, and an atmosphere electrode 6 and an exhaust electrode 8 that are a pair of electrodes made of platinum or the like, disposed to sandwich the solid electrolyte membrane 4 therebetween. An atmospheric chamber (not shown) into which external air flows is provided with the oxygen sensor 2. The atmosphere electrode is arranged so as to contact with the atmosphere in the atmospheric chamber on an opposite side to a face thereof that contacts with the solid electrolyte membrane 4. The oxygen sensor 2 is disposed in the exhaust passage of the internal combustion engine in a state in which the oxygen sensor 2 is housed in a case (unshown) having a plurality of vent holes. The exhaust electrode 8 of the oxygen sensor 2 is arranged so as to contact with exhaust gas that flows into the case from the plurality of vent holes.

As described above, the oxygen sensor 2 is, for example, disposed downstream of the catalyst disposed in the exhaust passage of the internal combustion engine. An electromotive force in accordance with a difference between the oxygen concentrations of the respective gases that the two electrodes 6 and 8 contact with arises in the oxygen sensor 2, and the electromotive force changes suddenly depending on which an air-fuel ratio is rich or lean relative to a theoretical air-fuel ratio. Accordingly, by detecting the electromotive force that arises in the oxygen sensor 2, it is possible to detect whether the exhaust gas downstream of the catalyst is rich or lean relative to the theoretical air-fuel ratio.

In this connection, the reactivity (detachment/adsorption properties) of $NO_x$ that is a lean gas component with respect to an electrode catalyst used in the oxygen sensor 2 is low. Consequently, the output sensitivity and responsiveness of the oxygen sensor 2 to lean gas are low. On the other hand, among rich gas components, $H_2$, $CH_4$, and CO, the rate of diffusion of $H_2$ and $CH_4$ is fast compared to the lean gas components ($NO_x$ and $O_2$), and the electrode adsorption properties of CO are high. Therefore, the sensitivity to rich gas of the oxygen sensor 2 is high. That is, the oxygen sensor 2 has a bias such that the oxygen sensor 2 is liable to output a rich output value and that the output sensitivity for lean gas thereof is low.

Since the oxygen sensor 2 is disposed in purified exhaust gas on the downstream side of the catalyst, the exhaust gas that is the detection object of the oxygen sensor 2 is very low concentration gas. In a case where the air-fuel ratio of the exhaust gas changes to a rich value or to a lean value under this kind of low concentration environment, a difference in the output sensitivity of the oxygen sensor 2 is large and is easily manifested, and consequently significant variations are liable to arise in the output of the oxygen sensor 2 due to the sensitivity difference. To suppress such kinds of variations in the sensitivity, according to Embodiment 1 of the present invention, the oxygen sensor 2 is subjected to the following processes at an initial stage of the oxygen sensor 2 (state in which the oxygen sensor 2 has not been used, such as before shipment).

FIG. 2 and FIG. 3 are views for describing a voltage that is applied between the electrodes 6 and 8 in the respective processes described below. FIG. 5a shows an embodiment of a control device 10a including a rich operation continuation time detector 11, a voltage application time period setter 12, and a voltage applicator 13. FIG. 5b shows an embodiment of a control device 10b including a lean operation continuation time detector 21, a voltage application time period setter 12, and a voltage applicator 13. FIG. 5c shows an embodiment of a control device 10c including a rich operating state detector 31, a voltage application time period setter 12, and a voltage applicator 13. FIG. 5d shows an embodiment of a control device 10d including a fuel-cut operation detector 41, a voltage application time period setter 12, and a voltage applicator 13. FIG. 5e shows an embodiment of a control device 10e including a rich operation continuation time detector 11, a voltage application time period setter 12, and a voltage applicator 13, and an element-resistance detector 14.

[Application of Alternating Voltage]

To stabilize the electrode interfaces of the oxygen sensor, first, an alternating voltage as illustrated in FIG. 2 is applied between the electrodes 6 and 8. As a result, adsorbates or contaminants of the electrodes are removed. In this case, the alternating voltage is applied by applying voltages of the same size and different polarities for the same time period one time or, as indicated by the dashed line in FIG. 2, repeatedly for a plurality of times. However, the alternating voltage is applied so that the voltage sizes and the application time periods are the same on the positive side and the negative side.

In this case, if the applied voltage is large, oxygen will be emitted from the zirconia of the solid electrolyte membrane 4 and the structural organization thereof will break down and become brittle, and so-called "blackening" will occur. Therefore, the size of the voltage during applying the alternating voltage is set to a level at which blackening does not occur. The size of the voltage the time period and the number of times of energization, when applying the alternating voltage, are set to optimal values for stabilizing the oxygen sensor 2 while preventing the occurrence of blackening. These values are previously determined by experiments or the like, and are stored in the control device.

An element temperature when applying the alternating voltage is set to a temperature within a range of 500° C. to 900° C. This is the temperature range that is actually used when the oxygen sensor 2 is installed in the internal combustion engine, and the temperatures of this temperature range are within the usage criteria of the oxygen sensor 2.

According to Embodiment 1, at an initial stage of the oxygen sensor 2, application of the above described alternating voltage is performed and, in addition, either one of the following activation processes, namely, a process for improving lean sensitivity and a process for suppressing rich sensitivity is also performed.

[Unidirectional Voltage Application for Suppressing Sensitivity Variations]

(a) Process for Improving Lean Sensitivity

As described above, the output sensitivity and responsiveness of the oxygen sensor 2 with respect to lean gas components are low. Accordingly, when it is required to detect a lean component with high sensitivity in an environment in which the oxygen sensor 2 is used, beforehand, as shown in FIG. 3, at an initial stage of the oxygen sensor 2, a voltage that makes the atmosphere electrode 6 positive and makes the exhaust electrode 8 negative is applied between the electrodes 6 and 8 of the oxygen sensor 2.

As a result, a large number of oxygen ions ($O^{2-}$) move to the atmosphere electrode 6 side. Consequently, a state can be entered in which movement of oxygen ions from the atmosphere electrode 6 to the exhaust electrode 8 is more liable to occur in comparison to the movement of opposite direction. Accordingly, the sensitivity of the oxygen sensor 2 to lean gas can be improved.

(b) Process for Suppressing Rich Sensitivity

On the other hand, the sensitivity of the oxygen sensor 2 with respect to rich gas is high, and the responsiveness is fast. Accordingly, when it is desired to suppress a bias in the sensitivity of the oxygen sensor 2 by suppressing the sensitivity to rich components in consideration of the environment in which the oxygen sensor 2 is to be used, a voltage to make the atmosphere electrode 6 negative and to make the exhaust electrode 8 positive is applied between the electrodes 6 and 8 of the oxygen sensor 2.

As a result, as shown in FIG. 1, a state is entered in which oxygen ions ($O^{2-}$) have moved from the atmosphere electrode 6 side to the exhaust electrode 8 side. By performing this process, a state in entered in which the oxygen ions are biased towards the exhaust electrode 8 side. Consequently, the sensitivity to rich gas is suppressed to a certain extent, and the bias in the sensitivity of the oxygen sensor 2 is eliminated.

Note that, the above described unidirectional voltage applications (a) and (b) should each satisfy the following conditions (c) to (f).

(c) The size of the applied voltage is such that blackening does not occur.

(d) The voltage of (a) or (b) is smaller than the above described alternating voltage.

(e) A value obtained by multiplying an absolute value of the voltage of (a) or (b) by the voltage application time period is set so as to be larger than a value obtained by multiplying an absolute value of the voltage on the positive side or negative side of the alternating voltage by the voltage application time period on the positive side or negative side.

(f) An element temperature at the time of voltage application is from 500° C. to 900° C.

Application of an alternating voltage stabilizes electrodes by changing the structure of the electrodes. Nevertheless, it is considered that if a voltage that is larger than the alternating voltage is applied when applying a unidirectional voltage for a process to suppress sensitivity variations that is performed thereafter, a further structural change or the like in the electrodes will occur, and the electrode stabilization effect produced by application of the alternating voltage will no longer be obtained. Accordingly, the unidirectional energization in the process to suppress sensitivity variations is set to a voltage that is less than the alternating voltage.

In addition, an object of the process for suppressing sensitivity variations is to cause the movement of electrical charges in the solid electrolyte membrane 4 to be as settled as possible in a certain direction (settled at an interface between the electrode 6 or 8 and the solid electrolyte membrane 4). Therefore, in the unidirectional energization for the process to suppress sensitivity variations, since it is necessary to secure a time period of a certain degree, voltage application is performed at a low voltage for a comparatively long time period.

As described above, depending on the environment in which the oxygen sensor 2 of Embodiment 1 is to be used, the oxygen sensor 2 is subjected to either a process for improving the lean sensitivity or a process for suppressing the rich sensitivity thereof. It is thereby possible to inhibit a bias in the sensitivity of the oxygen sensor 2 and suppress variations in the output of the oxygen sensor 2. Accordingly, changes in the air-fuel ratio of exhaust gas can be stably detected with higher accuracy.

For example, in a case where the OSC (oxygen storage capacity) of a catalyst is low, such as when a catalyst that has a low precious metal content is used, to improve controllability with respect to the air-fuel ratio, it is necessary to detect the air-fuel ratio with higher sensitivity and higher accuracy. In this respect, a process that suppresses variations in the sensitivity of the oxygen sensor by the above described control of the oxygen sensor 2 is effective.

According to the foregoing Embodiment 1, a case was described in which, after application of the alternating voltage, unidirectional energization is performed to improve the lean sensitivity or suppress the rich sensitivity. It is thereby possible to improve the stability of the characteristics of the oxygen sensor 2 for a longer term and to lessen long-term variations in the output of the oxygen sensor 2. However, an oxygen sensor according to the present invention is not limited thereto, and a configuration may be adopted in which only unidirectional energization is performed, and application of an alternating voltage is not performed.

Further, the configuration of the oxygen sensor 2 shown in FIG. 1 illustrates one example of the oxygen sensor 2. The present invention is not limited to the oxygen sensor 2 shown in FIG. 1, and the present invention can be applied to other electromotive force-type oxygen sensors.

Embodiment 2

It is considered that the ease of movement of oxygen ions and the bias of electric charges in the oxygen sensor 2 vary according to the usage environment of the oxygen sensor 2. Accordingly, it is considered that the effect of suppressing sensitivity variations by application of a unidirectional voltage described in Embodiment 1 is an effect that varies according to the usage environment. Therefore, according to Embodiment 2, when the internal combustion engine stops, a process for suppressing sensitivity variations is executed in accordance with the operating state of the internal combustion engine during a period from the previous time that the internal combustion engine stopped until the current time that the internal combustion engine stops, to thereby maintain the activation effect of the oxygen sensor 2.

Specifically, in the case of using the oxygen sensor 2 that has been subjected to the process for improving lean sensitivity of (a), when the air-fuel ratio of the exhaust gas is rich, there is a tendency for the effect of the process for improving the lean sensitivity to lessen. Accordingly, in the case of using the oxygen sensor 2 that has been subjected to the process for improving lean sensitivity of (a), the following control is executed under a usage environment of the oxygen sensor 2.

If the air-fuel ratio tended to be rich in the operating environment from the previous start-up of the internal combustion engine until the current time that the internal combustion engine stopped, application of a unidirectional voltage for improving the lean sensitivity is performed in a similar manner to the above described (a). That is, a voltage of a predetermined size is applied that makes the atmosphere electrode 6 positive and makes the exhaust electrode 8 a negative electrode. However, the size of the voltage at this time is set to a voltage that is smaller than a voltage that is applied in the initial process of the above described (a).

The voltage application time period is set in accordance with a continuation time during which operation under which the air-fuel ratio was rich continued (continuation time of rich operation) with respect to the previous operating conditions. Specifically, the longer that the continuation time of rich operation is, the longer the time period that is set as the voltage application time period.

Note that an optimal relationship of the voltage application time period with respect to the continuation time of rich operation is previously determined by experiments or the like. The relationship is stored in the control device as a map, and in the actual control, the voltage application time period is set in accordance with the respective continuation time.

FIG. 4 is a flowchart for describing a routine of control that the control device executes according to Embodiment 2 of the present invention. Specifically, according to the routine shown in FIG. 4, first, it is determined whether or not an instruction to stop the internal combustion engine has been detected (S102). If stopping of the internal combustion engine is not recognized, the current processing ends.

In step S102, if an instruction to stop the internal combustion engine is recognized, next, a continuation time of rich operation during the operation period of the internal combustion engine from the previous start-up of the internal combustion engine until the current time that the internal combustion engine stopped is detected (S104). In this case, the continuation time of rich operation is an integrated value of time in which an oxygen excess ratio λ that is determined by air-fuel ratio control is less than 1 during the aforementioned operation period, and this value is determined by the control device.

Next, a voltage application time period is set in accordance with the continuation time of rich operation (S106). The relationship between the voltage application time period and the continuation time of rich operation is determined in accordance with the map that is previously stored in the control device.

Subsequently, a predetermined voltage that makes the atmosphere electrode 6 positive and makes the exhaust electrode 8 negative is applied (S108). The voltage application time period at this time is set to the voltage application time period that has been set in step S106, and the other conditions for the voltage application are previously specified within a range that satisfies the conditions of (c) to (f) described above and stored in the control device. The sensitivity to lean gas can be improved by the application of a unidirectional voltage in this manner. Thereafter, the current processing ends.

As described above, according to Embodiment 2, it is also possible to appropriately maintain the effect of an initial process for improving the lean sensitivity in a case in which the usage environment of the oxygen sensor 2 is one in which the air-fuel ratio tends to be rich. Accordingly, variations in the oxygen sensor 2 that arise due to a sensitivity difference with respect to respective components of exhaust gas can be suppressed, and more accurate air-fuel ratio control can be realized.

Other Example of Embodiment 2

Although Embodiment 2 described an example relating to control in a usage environment in the case of using the oxygen sensor 2 that was subjected to the initial process of the above described (a), a rich sensitivity suppression effect of an initial process can be maintained in a similar manner with respect to the oxygen sensor 2 that was subjected to the initial process of the above described (b) also.

That is, when the atmosphere is one in which the air-fuel ratio of the exhaust gas is lean, there is a tendency for the effect of the initial process of (b), that is, a process for suppressing the rich sensitivity of the oxygen sensor 2 to lessen. Accordingly, when the oxygen sensor 2 that was subjected to the initial process of (b) is used, the following control is executed in a similar manner to the case of the initial process of (a) under the usage environment of the oxygen sensor 2.

If the air-fuel ratio tended to be lean in the operating environment from the previous start-up of the internal combustion engine until the current time that the internal combustion engine stopped, a voltage of a predetermined size is applied that makes the atmosphere electrode 6 negative and makes the exhaust electrode 8 positive. The voltage at this time is set to a voltage that is smaller than the voltage applied in the initial process of (b).

The voltage application time period is set in accordance with a time during which operation under which the air-fuel ratio was lean continued (continuation time of lean operation) with respect to the previous operating conditions of the internal combustion engine. Specifically, the longer that the continuation time of lean operation is, the longer the time period that is set as the voltage application time period.

The specific control can be executed in a similar manner as that described above by making the voltage application time period in step S106 in the routine shown in FIG. 4 a time period that is in accordance with a continuation time of lean operation, and making the direction of the voltage application in S108 a direction to make the atmosphere electrode 6 side negative.

According to Embodiment 2 a case was described in which a time period for application of a unidirectional voltage is set in accordance with a continuation time of rich operation or of lean operation. However, the present invention is not limited thereto. For example, a voltage application time period may be determined in accordance with an integrated value of a rich amount (or lean amount) in an operation period and a continuation time of rich operation (or of lean operation).

In addition, according to Embodiment 2 a case was described in which only the application of a unidirectional voltage for a process to suppress sensitivity variations is performed. However, the present invention is not limited thereto, and a configuration may also be adopted in which, similarly to the initial process described in Embodiment 1, application of an alternating voltage of a predetermined time period is performed prior to the process to suppress sensitivity variations. It is thereby possible to stabilize the characteristics of the oxygen sensor 2 for an even longer term.

Further, according to Embodiment 2 a case was described in which application of a voltage for a process to suppress sensitivity variations is executed in a state immediately after stopping of the internal combustion engine. However, in the present invention the timing for applying a voltage under a usage environment of the oxygen sensor 2 is not limited thereto. For example, in the present invention, application of a unidirectional voltage can be performed when starting the internal combustion engine. In this case, when the internal combustion engine stops, a continuation time of rich operation or an integrated value of a rich amount and a continuation time of rich operation c (alternatively, a continuation time of lean operation or an integrated value of a lean amount and a continuation time of lean operation) are stored in a backup RAM, and by reading out the relevant value at startup, control that is similar to the routine shown in FIG. 4 can be executed.

In addition, according to Embodiment 2 a case was described in which, during an operation period from the previous start-up of the internal combustion engine until the current stopping of the internal combustion engine, an integrated value of time in which rich operation (or lean operation) was performed is taken as a continuation time of rich (or lean) operation, and a voltage application time period is set in accordance therewith. However, in the present invention, setting of a voltage application time period is not limited thereto. For example, a configuration may also be adopted in which a certain operation period of the internal combustion engine is defined based on a running distance or a usage time period of the oxygen sensor 2 or the like, and time periods in which a rich operation (or a lean operation) was performed are integrated for each of the operation periods, and a voltage application time period is set in accordance therewith.

Furthermore, according to Embodiment 2 a case was described in which a process for lean sensitivity improvement or rich sensitivity suppression is performed each time the internal engine stops (or starts up). However, the present invention is not limited thereto. For example, a configuration can also be adopted in which, during a certain specified operation period, a situation where rich operation (or lean operation) was performed continuously for a predetermined time period that is long to a certain extent is detected, and a process for lean sensitivity improvement (or rich sensitivity suppression) is performed only when such a situation was detected. In addition, in this case, an application time period or the like may be set in accordance with the time for which the rich (or lean) operation continued.

Embodiment 3

As described above, the ease of movement of oxygen ions and the bias of electric charges in the oxygen sensor 2 vary according to the usage environment of the oxygen sensor 2, and therefore the effect of suppressing sensitivity variations by application of a unidirectional voltage in Embodiment 1 varies according to the usage environment. Therefore, according to Embodiment 3, in addition to applying a unidirectional voltage when the internal combustion engine stops (or starts up) as described in Embodiment 2, a process is also executed for suppressing sensitivity variations in accordance with the operating state during operation of the internal combustion engine.

Specifically, the effect for improving the lean sensitivity of (a) tends to lessen under an environment in which the air-fuel ratio of exhaust gas is more on the rich side. Accordingly, when the oxygen sensor 2 that has been subjected to the initial process of (a) is used, when the internal combustion engine is operating under a high speed/high load operating condition and in a rich amount increasing operation range, application of a unidirectional voltage for lean sensitivity improvement is additionally performed under a usage environment of the oxygen sensor 2.

Voltage application in the foregoing cases is performed in a manner that satisfies the conditions of (c) to (f) described above. Thus, changes in the structure or changes in the characteristics of the sensor from the initial state thereof by the voltage application is prevented. Further, the size of the applied voltage is made less than the voltage that is applied in the initial process of (a). The specific voltages that are applied and the application time periods in these cases are appropriately set in advance as the result of experiments or the like, and are stored in the control device.

In the specific control, when a predetermined condition is satisfied that indicates operation under a high speed and high load operating condition and in a rich amount increasing operation range during operation of the internal combustion engine, a voltage of a predetermined size is applied that makes the atmosphere electrode 6 positive and the exhaust electrode 8 negative for an application time period that is stored in the control device.

As described above, according to the control in Embodiment 3, when the oxygen sensor 2 that has been subjected to process for improving the lean sensitivity of (a) is used, a process for improving the lean sensitivity is additionally executed in accordance with the operating state. Therefore, the effect of the process for suppressing sensitivity variations in the oxygen sensor 2 can be maintained even in different operating environments.

Other Example of Embodiment 3

Although Embodiment 3 described an example relating to control during use of the oxygen sensor 2 in the case of using the oxygen sensor 2 that was subjected to the initial process of the above described (a), with respect to the oxygen sensor that was subjected to the initial process of the above described (b) also, the rich sensitivity suppression effect of the initial process can be maintained in a similar manner.

That is, under an environment in which an exhaust gas air-fuel ratio is more on the lean side, there is a tendency for the effect of the initial process of (b), that is, the effect of a process for suppressing the rich sensitivity of the oxygen sensor 2 to lessen. Accordingly, when the oxygen sensor 2 that was subjected to the initial process of (b) is used, application of a unidirectional voltage for suppressing rich sensitivity in a similar manner to the process of (b) is executed in a case where operation of the internal combustion engine has entered a fuel-cut operation range.

That is, during operation of the internal combustion engine, when a predetermined condition that indicates a fuel-cut operation is satisfied, a voltage of a predetermined size that makes the atmosphere electrode 6 negative and makes the exhaust electrode 8 positive is applied for a predetermined application time period. Note that, in this case also, the conditions (c) to (f) are satisfied by the voltage application. Further, the size of a voltage that is applied by this control is set so as to be smaller than a voltage applied in the initial process of (b).

In this connection, in the description of the control of Embodiment 3, an example was described in which a voltage of a predetermined size is applied once for a predetermined time period. However, a method of applying the voltage is not limited thereto and, for example, a method may be adopted that intermittently applies a unidirectional voltage. That is, a configuration may be adopted in which a process of applying a voltage and thereafter stopping the voltage application is repeatedly performed a predetermined number of times such as, for example, applying a voltage for 0.5 seconds and stopping application of the voltage for 0.5 seconds.

Further, in the description of the control of Embodiment 3, an example was described in which application of a unidirectional voltage is only executed when an operating condition of the internal combustion engine satisfies a predetermined condition. However, the present invention is not limited thereto, and a configuration may also be adopted in which application of an alternating voltage as described in Embodiment 1 is performed prior to application of a unidirectional voltage.

Embodiment 4

According to Embodiment 4, voltage application is performed in accordance with deterioration over time or the like of the oxygen sensor 2. In the oxygen sensor 2, element resistance increases due to deterioration over time, heat deterioration and the like. As a result, even though application of a voltage is performed in the same manner, the amount of current that flows between the electrodes 6 and 8 of the oxygen sensor 2 gradually decreases. Therefore, it is considered that when the control described in the foregoing Embodiments 2 and 3 is performed with the same voltage value and for the same voltage application time period, the effect thereof gradually decreases.

In this respect, according to the system of Embodiment 4, first, a change in the element resistance is detected. The element resistance can be estimated based on an average heater electric power amount at the time of sensor element temperature control. A voltage and an application time period for the alternating voltage application as well as a voltage and an application time period for the process to suppress sensitivity variations are set so as to increase as the element resistance increases. However, in this case also, the relevant values are set so as to satisfy the conditions of (c) to (f) that are described in Embodiment 1.

The optimal relationship between this kind of element resistance and an applied voltage and application time period is previously determined by experiments or the like for each oxygen sensor 2. The relationship is stored as a map in the control device. In the specific control, the element resistance is estimated, and an applied voltage or application time period that is in accordance with the element resistance is determined based on the map.

As described above, according to the control of Embodiment 4, even when element resistance due to deterioration over time or the like increases, by increasing the application time period or applied voltage, it is possible to obtain an effect that improves the lean sensitivity or suppresses the rich sensitivity by performing a process to suppress sensitivity variations.

It is to be understood that even when the number, quantity, amount, range or other numerical attribute of an element is mentioned in the above description of the embodiments, the present invention is not limited to the mentioned numerical attribute unless it is expressly stated or theoretically defined. Further, structures and steps and the like described in conjunction with the embodiments are not necessarily essential to the present invention unless expressly stated or theoretically defined.

DESCRIPTION OF NOTATIONS

2 oxygen Sensor
4 solid electrolyte membrane
6 atmosphere electrode
8 exhaust electrode
10a, 10b, 10c, 10d, 10e control device
11 rich operation continuation time detector
12 voltage application time period setter
13 voltage applicator
14 element-resistance detector
21 lean operation continuation time detector
31 rich operating state detector
41 fuel-cut operation detector

The invention claimed is:

1. An oxygen sensor controller for an electromotive force-type oxygen sensor disposed in an exhaust passage of an internal combustion engine, the oxygen sensor comprising:
   a solid electrolyte;
   an atmosphere electrode that is disposed on one face side of the solid electrolyte and contacts with atmosphere when disposed in the exhaust passage; and an exhaust electrode that is disposed on a face on an opposite side to the one face of the solid electrolyte and contacts with exhaust gas when disposed in the exhaust passage, the oxygen sensor being configured to be subjected to an activation process that applies a unidirectional voltage between the atmosphere electrode and the exhaust electrode, and the oxygen sensor controller being configured to:

apply a voltage in the same direction as the unidirectional voltage between the atmosphere electrode and the exhaust electrode in accordance with operating state of the internal combustion engine;

detect a continuation time of rich operation that is a time in which an air-fuel ratio is rich relative to a theoretical air-fuel ratio during a predetermined operation period of the internal combustion engine;

set a voltage application time period in accordance with the continuation time of rich operation; and in accordance with the voltage application time period set in accordance with the continuation time of rich operation, apply the unidirectional voltage between the atmosphere electrode and the exhaust electrode to make the atmosphere electrode positive and make the exhaust electrode negative.

2. An oxygen sensor controller for an electromotive force-type oxygen sensor disposed in an exhaust passage of an internal combustion engine, the oxygen sensor comprising:

a solid electrolyte;

an atmosphere electrode that is disposed on one face side of the solid electrolyte and contacts with atmosphere when disposed in the exhaust passage; and an exhaust electrode that is disposed on a face on an opposite side to the one face of the solid electrolyte and contacts with exhaust gas when disposed in the exhaust passage, the oxygen sensor being configured to be subjected to an activation process that applies a unidirectional voltage between the atmosphere electrode and the exhaust electrode, and the oxygen sensor controller being configured to:

apply a voltage in the same direction as the unidirectional voltage between the atmosphere electrode and the exhaust electrode in accordance with operating state of the internal combustion engine;

detect a continuation time of lean operation that is a time in which an air-fuel ratio is lean relative to a theoretical air-fuel ratio during a predetermined operation period of the internal combustion engine;

set a voltage application time period in accordance with the continuation time of lean operation; and in accordance with the voltage application time period set in accordance with the continuation time of lean operation, apply the unidirectional voltage between the atmosphere electrode and the exhaust electrode to make the atmosphere electrode negative and make the exhaust electrode positive.

3. An oxygen sensor controller for an electromotive force-type oxygen sensor disposed in an exhaust passage of an internal combustion engine, the oxygen sensor comprising:

a solid electrolyte;

an atmosphere electrode that is disposed on one face side of the solid electrolyte and contacts with atmosphere when disposed in the exhaust passage; and an exhaust electrode that is disposed on a face on an opposite side to the one face of the solid electrolyte and contacts with exhaust gas when disposed in the exhaust passage, the oxygen sensor being configured to be subjected to an activation process that applies a unidirectional voltage between the atmosphere electrode and the exhaust electrode, and the oxygen sensor controller being configured to:

apply a voltage in the same direction as the unidirectional voltage between the atmosphere electrode and the exhaust electrode in accordance with operating state of the internal combustion engine, detect a rich operating state that is a state in which an operating state of the internal combustion engine is in a predetermined high speed and high load operating range and in which an air-fuel ratio is in a rich amount increasing range, and when the rich operating state is detected, apply the unidirectional voltage between the atmosphere electrode and the exhaust electrode to make the atmosphere electrode positive and make the exhaust electrode negative.

4. An oxygen sensor controller for an electromotive force-type oxygen sensor disposed in an exhaust passage of an internal combustion engine, the oxygen sensor comprising:

a solid electrolyte;

an atmosphere electrode that is disposed on one face side of the solid electrolyte and contacts with atmosphere when disposed in the exhaust passage; and an exhaust electrode that is disposed on a face on an opposite side to the one face of the solid electrolyte and contacts with exhaust gas when disposed in the exhaust passage, the oxygen sensor being configured to be subjected to an activation process that applies a unidirectional voltage between the atmosphere electrode and the exhaust electrode, and the oxygen sensor controller being configured to:

apply a voltage in the same direction as the unidirectional voltage between the atmosphere electrode and the exhaust electrode in accordance with operating state of the internal combustion engine;

detect when an operating state of the internal combustion engine in which the oxygen sensor is disposed is a fuel-cut operation state, and when the fuel-cut operation state is detected, apply the unidirectional voltage between the atmosphere electrode and the exhaust electrode to make the atmosphere electrode negative and make the exhaust electrode positive.

5. The oxygen sensor controller according to claim 1, wherein the unidirectional voltage is a voltage in a range which does not cause blackening with respect to the solid electrolyte.

6. The oxygen sensor controller according to claim 1, wherein the oxygen sensor controller is configured to:

detect or estimate an element resistance of the oxygen sensor; and control a size of the unidirectional voltage or an application time period of the unidirectional voltage in accordance with the element resistance.

7. The oxygen sensor controller according to claim 2, wherein the unidirectional voltage is a voltage in a range which does not cause blackening with respect to the solid electrolyte.

8. The oxygen sensor controller according to claim 2, wherein the oxygen sensor controller is configured to:
   detect or estimate an element resistance of the oxygen sensor; and
   control a size of the unidirectional voltage or an application time period of the unidirectional voltage in accordance with the element resistance.

9. The oxygen sensor controller according to claim 3, wherein the unidirectional voltage is a voltage in a range which does not cause blackening with respect to the solid electrolyte.

10. The oxygen sensor controller according to claim 3, wherein the oxygen sensors controller is configured to:
    detect or estimate an element resistance of the oxygen sensor; and
    control a size of the unidirectional voltage or an application time period of the unidirectional voltage in accordance with the element resistance.

11. The oxygen sensor controller according to claim 4, wherein the unidirectional voltage is a voltage in a range which does not cause blackening with respect to the solid electrolyte.

12. The oxygen sensor controller according to claim 4, wherein the oxygen sensor controller is configured to:
    detect or estimate an element resistance of the oxygen sensor; and
    control a size of the unidirectional voltage or an application time period of the unidirectional voltage in accordance with the element resistance.

\* \* \* \* \*